(12) United States Patent
Schaller et al.

(10) Patent No.: US 10,448,984 B2
(45) Date of Patent: Oct. 22, 2019

(54) HUMERAL HEAD FIXATION DEVICE FOR OSTEOPOROTIC BONE

(71) Applicant: DePuy Synthes Products, Inc., Raynham, MA (US)

(72) Inventors: Konrad Schaller, Grenchen (CH); Alfred Niederberger, Salzburg (AT); Johann Fierlbeck, Salzburg (AT)

(73) Assignee: DePuy Synthes Products, Inc., Raynham, MA (US)

( * ) Notice: Subject to any disclaimer, the term of this patent is extended or adjusted under 35 U.S.C. 154(b) by 223 days.

(21) Appl. No.: 15/371,355

(22) Filed: Dec. 7, 2016

(65) Prior Publication Data

US 2017/0079703 A1  Mar. 23, 2017

Related U.S. Application Data

(63) Continuation of application No. 12/856,983, filed on Aug. 16, 2010, now Pat. No. 9,539,039.

(Continued)

(51) Int. Cl.
*A61B 17/86* (2006.01)
*A61B 17/72* (2006.01)
(Continued)

(52) U.S. Cl.
CPC ...... *A61B 17/8685* (2013.01); *A61B 17/7266* (2013.01); *A61B 17/746* (2013.01);
(Continued)

(58) Field of Classification Search
None
See application file for complete search history.

(56) References Cited

U.S. PATENT DOCUMENTS 3,791,380 A * 2/1974 Dawidowski ........ A61B 17/746
606/68
5,603,715 A  2/1997 Kessler
(Continued)

FOREIGN PATENT DOCUMENTS

EP  1 836 981  9/2007
JP  2007/518537  7/2007
(Continued)

*Primary Examiner* — Anu Ramana
(74) *Attorney, Agent, or Firm* — Fay Kaplun & Marcin, LLP

(57) ABSTRACT

A device includes an elongated body configured to be coupled to a bone stabilization implant so that, when the bone stabilization implant is mounted to a target bone, the body extends away from the bone stabilization implant at an angle selected so that the elongated body passes into a target portion of bone. The body defines a lumen therein extending to an opening in a distal end of the body. The device also includes a deploying member housed within the lumen of body for movement between a first position and a second position. In addition, the device includes a plurality of wires coupled to the deploying member so that movement of the deploying member through the lumen moves the wires between an insertion position and a deployed position in which the distal ends of the wires penetrate a portion of bone adjacent to the distal end of the body.

8 Claims, 4 Drawing Sheets

Related U.S. Application Data

(60) Provisional application No. 61/242,093, filed on Sep. 14, 2009.

(51) Int. Cl.
    *A61B 17/74*     (2006.01)
    *A61B 17/80*     (2006.01)
    *A61B 17/00*     (2006.01)

(52) U.S. Cl.
    CPC ........ *A61B 17/8061* (2013.01); *A61B 17/864* (2013.01); *A61B 17/8635* (2013.01); *A61B 2017/00867* (2013.01)

(56) References Cited

U.S. PATENT DOCUMENTS

| | | |
|---|---|---|
| 5,849,004 A | 12/1998 | Bramlet |
| 6,077,264 A | 6/2000 | Chemello |
| 6,558,388 B1 | 5/2003 | Bartsch et al. |
| 2007/0233105 A1 | 10/2007 | Nelson et al. |
| 2010/0152786 A1* | 6/2010 | Behrbalk ............... A61B 17/68 606/301 |

FOREIGN PATENT DOCUMENTS

| | | |
|---|---|---|
| KR | 10-2004-0002891 | 6/2008 |
| WO | 01/28443 | 4/2001 |
| WO | 2002/078555 | 10/2002 |
| WO | 03/007830 | 1/2003 |
| WO | 2005/072284 | 8/2005 |

* cited by examiner

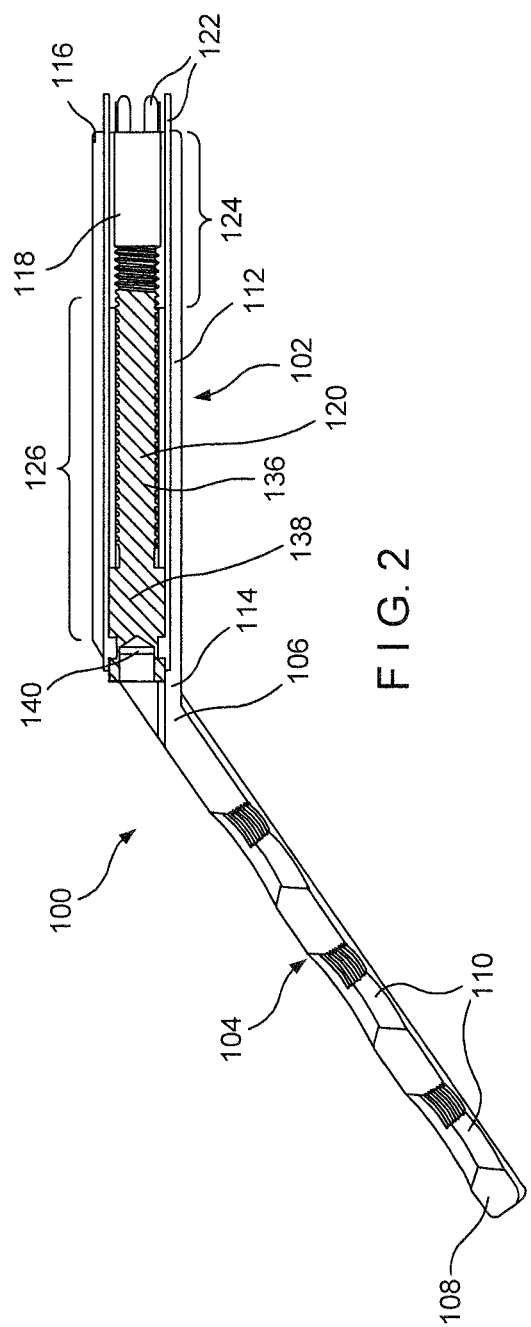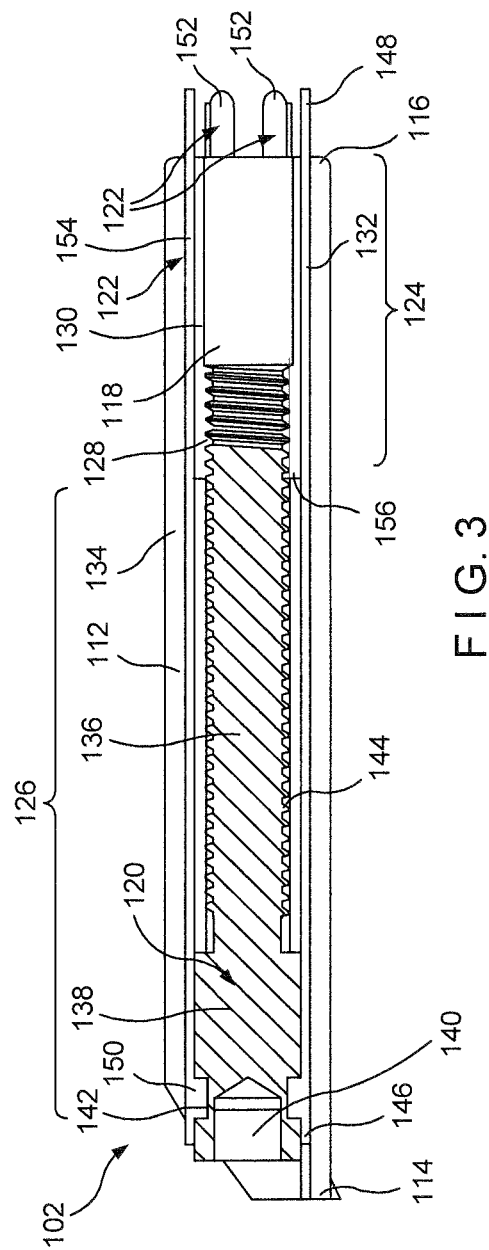

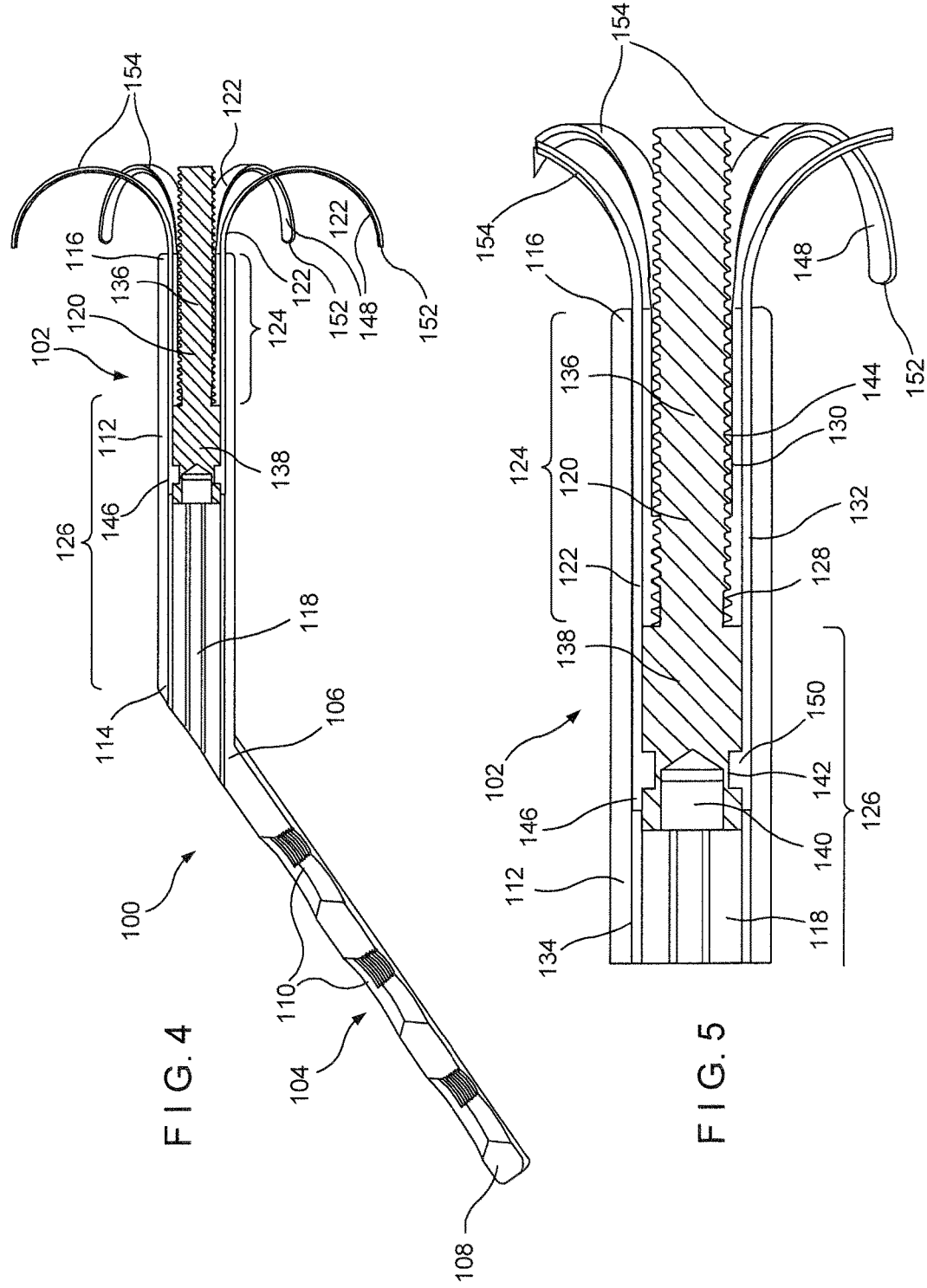

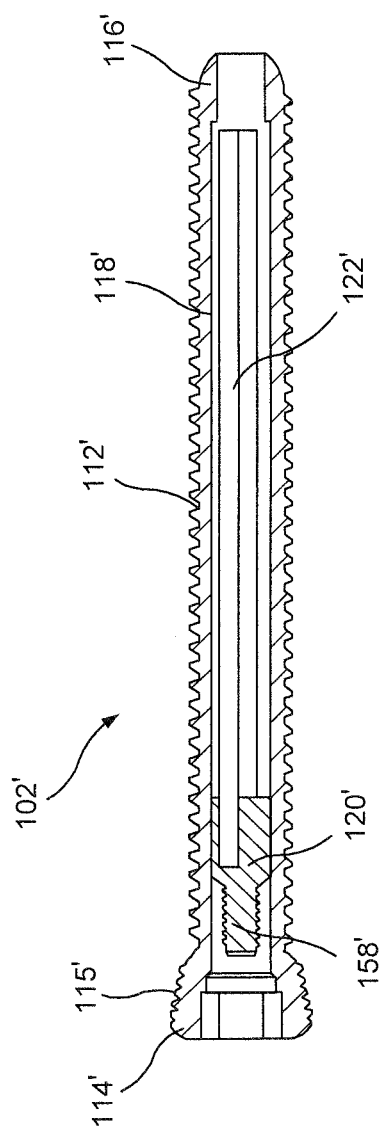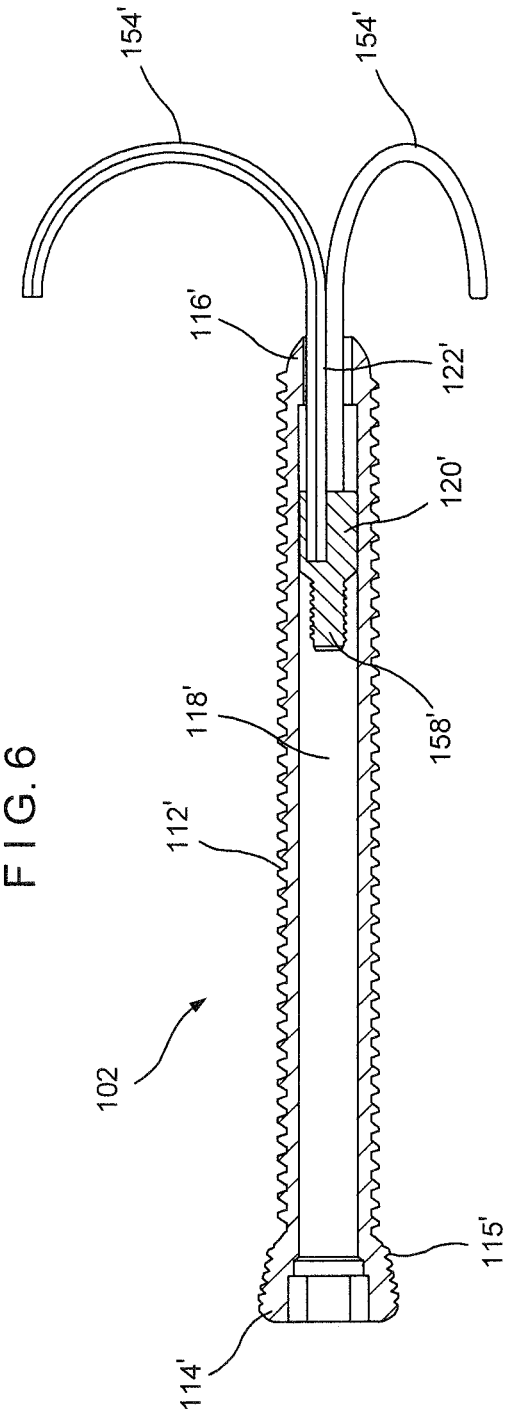

HUMERAL HEAD FIXATION DEVICE FOR OSTEOPOROTIC BONE

PRIORITY CLAIM

The present application is a Continuation application of U.S. patent application Ser. No. 12/856,983 filed Aug. 16, 2010, now U.S. Pat. No. 9,539,039, which claims priority to U.S. Provisional patent application Ser. No. 61/242,093 filed Sep. 14, 2009. The disclosures of these applications and/or patents are incorporated herein by reference.

FIELD OF THE INVENTION

The present invention relates to the treatment of a bone and, in particular, to a system and method for treating an osteoporotic bone using pre-shaped wires that penetrate the bone when a force is exerted on proximal ends of the wires.

BACKGROUND

Treatment of proximal and distal bone fractures can be very challenging in elderly patients with osteoporotic bones since implants cannot be fixed to the bone in a stable manner. Operative techniques used for treating proximal and distal bone fractured often result in complications such as malunion, non-union, osteonecrosis of the epiphysis, loosening of screws and/or loss of reduction.

SUMMARY OF THE INVENTION

The present invention relates to a device for treating a bone, comprising an elongated body configured to be coupled to a bone plate so that, when the bone plate is mounted to a target bone in a desired position, the elongated body extends away from the bone plate at an angle selected so that the elongated body passes into a target portion of bone along a desired path. The elongated body defines a lumen therein extending to an opening in a distal end of the elongated body. In addition, the device includes a deploying member housed within the lumen of elongated body for movement between a first position and a second position. The device also includes a plurality of wires coupled to the deploying member so that movement of the deploying member through the lumen moves the wires between an insertion position in which distal ends of the wires are housed within the lumen and a deployed position in which the distal ends of the wires extend distally out of the opening in the distal end of the elongated body to penetrate a portion of bone adjacent to the distal end of the elongated body. The wires are biased to assume an anchoring shape when extended out of the elongated body.

BRIEF DESCRIPTION OF THE DRAWINGS

FIG. 2 shows a cross-sectional side view of the system of FIG. 1, in a first configuration;

FIG. 3 shows a cross-sectional side view of a device of the system of FIG. 1, in the first configuration;

FIG. 4 shows a cross-sectional side view of the system of FIG. 1, in a second configuration;

FIG. 5 shows a cross-sectional side view of a distal portion of the device of FIG. 3, in the second configuration;

FIG. 6 shows a cross-sectional side view of a device according to an alternate embodiment of the present invention, in a first configuration; and FIG. 7 shows a cross-sectional side of the device of FIG. 6, in a second configuration.

DETAILED DESCRIPTION

Figure 1:
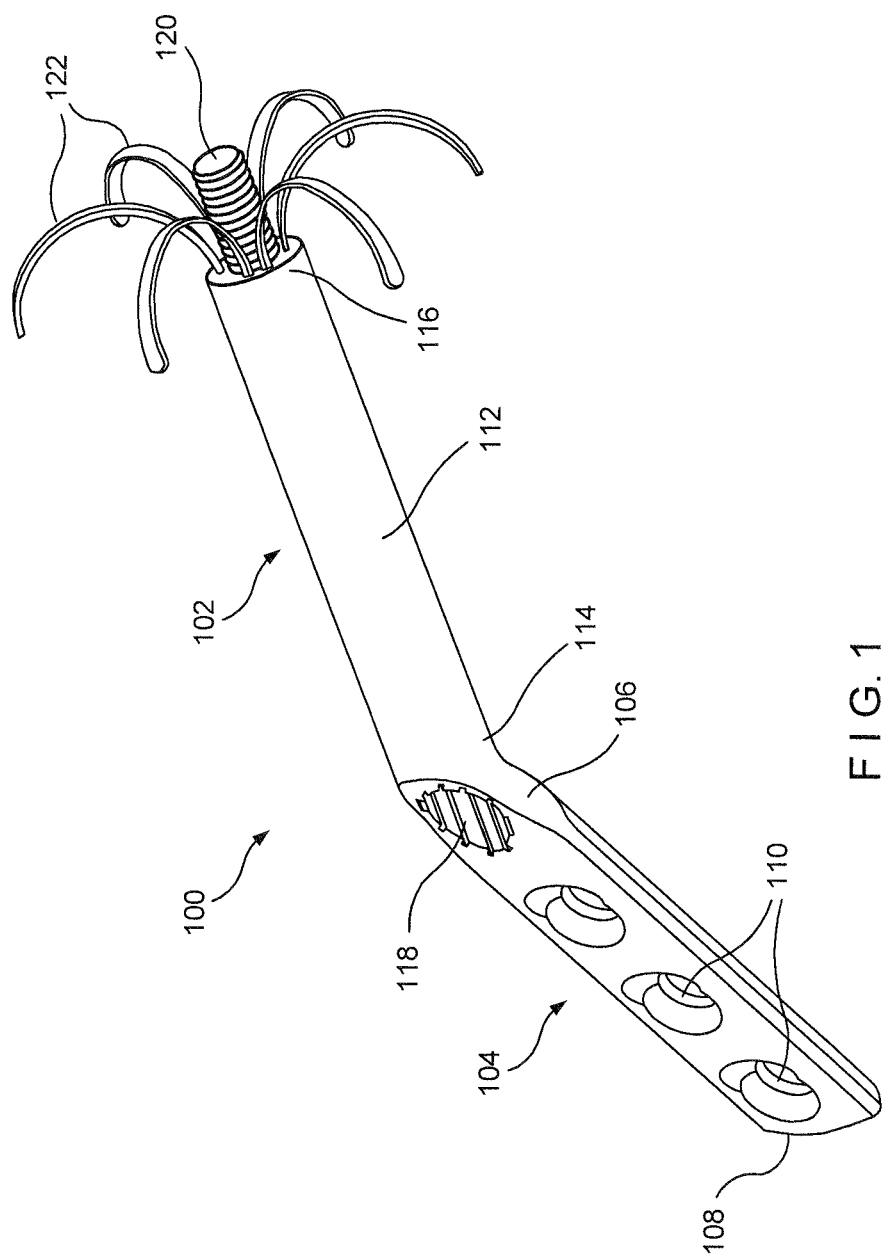
FIG. 1 shows a perspective view of a system according to an exemplary embodiment of the present invention.

The present invention may be further understood with reference to the following description and the appended drawings, wherein like elements are referred to with the same reference numerals. The present invention relates to the treatment of a bone, particularly, the treatment of an osteoporotic bone that may be difficult to fix. Exemplary embodiments of the present invention describe a system and method for treating the bone using pre-shaped wires that penetrate the bone when a force is exerted on proximal ends of the wires. Although exemplary embodiments described specifically relate to the treatment of fractures of the upper humerus, it will be understood by those of skill in the art that the present invention may be used to treat any bone in the body. It should also be noted that the terms proximal and distal, as used herein, are intended to describe a direction towards (proximal) and away from (distal) a surgeon or other user of the device.

As shown in FIGS. 1-5, a system 100 according to an exemplary embodiment of the invention comprises a device 102 coupleable to or integrally formed with a longitudinal plate 104 for fixing a fracture of a hone, such as a femur or humerus. As shown in FIG. 1, the device 102 is coupled to a first end 106 of the plate 104 and extends away from the end 106 at an angle relative to a longitudinal axis of the plate 104 selected so that, when the plate 104 is mounted at a desired position on a target bone, the device 102 extends along a desired path into a head portion of the target bone. The plate 104 extends from the first end 106 to a second end 108 and includes a plurality of openings 110 along a length thereof for receiving bone fixation elements to fix the plate 104 to the target bone. Although the device 102 is shown integrally formed with the plate 104, it will be understood by those of skill in the art that in an alternative embodiment, a device 102', as shown in FIGS. 6-7, may be formed as a separate component configured to be coupled to the plate 104, a nail or other anchoring element. For example, the device 102' may be inserted into the bone via an opening in the plate 104. Since the device 102' is a separate component, it will be understood by those of skill in the art that a proximal end 114' of the device 102' is configured to be coupled to the plate 104. The device 102' will be described in further detail below. It will also be understood by those of skill in the art that although the device 102 is shown as attached to the first end 106 of the plate 104, the device 102 may be attached or engaged to any point along a length of the plate 104 so long as, when the plate 104 is coupled to the target bone in a desired position, the device 102 extends into the head of the bone along a desired path.

The device 102 further comprises an elongated body 112 housing a bolt 120 and a plurality of wires 122 which, in an insertion configuration, are received within the body 112 and which are movable to a deployed configuration in which they extend out of the body 112 into the head portion of the target bone. The elongated body 112 extends from a proximal end 114 to a distal end 116 and includes a lumen 118 extending therethrough. The proximal end 114 of the elongated body 112 is attached or engaged to the plate 104 such that the plate 104 may be positioned externally to the target bone while the elongated body 112 extends into the bone.

The lumen 118 is sized and shaped to accommodate the bolt 120 and the plurality of wires 122 such that the bolt 120 and the plurality of wires 122 are longitudinally movable relative to the elongated body 112. In the insertion configuration, shown in FIGS. 2-3, the wires 122 are housed substantially within the lumen 118. Rotation of the bolt 120 about a longitudinal axis of the device 102 moves the plurality of wires 122 along the longitudinal axis, distally relative to the elongated body 112 into the deployed configuration shown in FIGS. 4-5.

As shown in FIGS. 2-5 specifically, each of the wires 122 extends longitudinally from a proximal end 146 including a protrusion 150 extending radially inward to couple to the groove 142 of the head 138 of the bolt 120 such that the plurality of wires 122 are spaced circumferentially about the bolt 120. The wires 122 and the bolt 120 are rotatably coupled to one another such that the wires 122 do not rotate as the bolt 120 is rotated through the elongated body 112. Distal ends 148 of the wires 122 preferably include a bone penetrating tip 152 which may be sharpened or otherwise treated to facilitate penetration of the spongious bone by the wires 122. As seen in FIG. 5, in the deployed configuration, distal portions of wires 122 extend distally out of the distal end 116 of the elongated body 112 to penetrate the head portion of a target bone into which the device 102 has been inserted. In this embodiment, the wires 122 are biased so that, upon exiting the body 112, they move toward a memorized shape in which they extend distally away from the distal end 116 for a distance and then bend back proximally to anchor the device 102 in the target bone. For example, the wires 122 may be formed of a shape memory material such as nitinol. Wires 122 formed of such a material may be pre-shaped into the bent configuration, in which a distal portion 154 of the wire is curved through between approximately 90° and 180°. In the insertion configuration, the wires 122 are held in a substantially straight configuration within the elongated body 112. However, as the wires 122 are moved to the deployed configuration, the distal portions 154 extend past the distal end 116 of the elongated body 112 and revert to the bent configuration as the sharp tip 152 pierces through the bone. The number of wires 122 and the circumferential orientation of the wires 122 may vary depending on specific patient issues and a load carrying capacity of the device 102.

As the wires 122 move to the deployed configuration along these curved paths, a length of the wires 122 within the bone is increased while preventing the wires 122 from too closely approaching an outer surface of the head portion of the target bone. It will be understood by those of skill in the art that this bending of the wires 122 away from the outer surface of the head portion results in a high load-bearing, umbrella-shaped fixation resisting movement of the device 102 after the wires 122 have been implanted in the target bone. The sharp tip 152 pierces through the bone to form a recess that is substantially the same shape and size as the wires 122, resulting in a stable interface. Furthermore, the bent configuration guides the wires 122 away from cartilage in a joint area of the bone, preventing damage to the joint surfaces. The bent configuration also facilitates the dynamic behavior necessary for a smooth transition of compression and shear forces. Thus, it will be understood by those of skill in the art that moving the plurality of wires 122 from the insertion configuration to the deployed configuration enhances the stability and fixation of the device 102 within the target bone.

A thickness of a wall of the distal portion 124 of the elongated body 112 is greater than a thickness of a wall of a proximal portion 126 of the elongated body 112 such that a portion of the lumen 118 extending through the distal portion 124 is greater in diameter than a portion of the lumen 118 extending through the proximal portion 126. The distal portion 124 includes a threading 128 along at least a portion of an inner surface 130 thereof for engaging with a shaft 136 of the bolt 120. The distal portion 124 may further include a plurality of openings 132 extending along a length of the distal portion 124 and longitudinally aligning with an inner surface 134 of the proximal portion 126 of the elongated body 112 such that each of the wires 122 may extend along the inner surface 134 into one of the openings 132. Thus, it will be understood by those of skill in the art that the openings 132 are sized and shaped to accommodate the wires 122.

The bolt 120 includes a head 138 and a shaft 136, extending distally therefrom. The head 138 includes a driving element 140 such as a hex-recess for engaging a driving tool to drive the bolt 120 distally through the lumen 118 of the elongated body 112 to move the wires between the insertion and deployed configurations. The head 138 further includes a groove 142 about a circumference thereof for coupling with proximal ends 146 of the wires 122. The shaft 136 includes a threading 144 along a length of the shaft 136 for engaging the threading 128 of the distal portion 124 of the elongated body 112. Thus, rotation of the bolt 120 about the longitudinal axis of the device 102 moves the device 102 between the insertion and deployed configurations. In the insertion configuration, the bolt 120 is substantially housed within the lumen 118 of the elongated body 112 while, in the deployed configuration, the distal end of the bolt 120 extends distally from the body 112. Furthermore, the bolt 120 may include a head 138 configured so that, when the device 102 moved to the deployed configuration, the head 138 abuts a proximal end 156 of the distal portion 124 of the elongated body 112 such that the bolt 120 cannot move further distally.

It will also be understood by those of skill in the art that the device 102 may be removed from the bone by rotating the bolt 120 about the longitudinal axis in a direction opposite the direction used to move the device 102 to the deployed configuration. This moves the bolt 120 proximally back into the elongated body 112 retracting the wires 122 along the curved paths through which they were deployed back into the lumen 118 to the insertion configuration. At this point, the device 102 is no longer anchored in the head portion of the target bone and may be removed therefrom as would be understood by those of skill in the art.

As shown in FIGS. 6-7, the device 102' may be substantially similar to the device 102, as described above in regard to the system 100. The device 102' may be a nail, screw or other anchoring element that is insertable into the head portion of the target bone via an opening in the plate 104. Similarly to the device 102, the device 102' includes an elongated body 112' that extends from a proximal end 114' to a distal end 116' with a lumen 118' extending therethrough. The lumen 118' is sized and shaped to accommodate a bolt 120' and a plurality of wires 122' such that the bolt 120' and the wires 122' are longitudinally movable relative to the lumen 118', between an insertion configuration, shown in FIG. 6, and a deployed configuration, shown in FIG. 7. The proximal end 114' of the elongated body 112' includes a coupling mechanism for coupling to the plate 104. For example, the proximal end 114' may include a threading 115' along an outer surface thereof for engaging a threading of the opening of the bone plate 104.

In the insertion configuration, the wires 122' are substantially housed within the elongated body 112'. Similarly to the bolt 120, the bolt 120' is movable relative to the elongated housing 112' to move the wires 122' into the deployed configuration in which distal portions 154' extend distally past the distal end 116' of the elongated housing 112' and into a head portion of the bone, following a curved path of the distal portions 154'. The bolt 120', however, is not rotated relative to the elongated housing 112' to deploy the wires 122'. The bolt 120' is non-rotatably coupled to a proximal end 146' of the wires 122'. The bolt 120' may further include a pin 158' at a proximal end thereof such that the pin 158' may be used to push the bolt 120' and the wires 122' distally through the lumen 118' and into the deployed configuration. To remove the device 102' from the bone, the bolt 120' may be drawn proximally through the lumen 118' via the pin 158', retracting the wires 122' back into the insertion configuration along the curved paths through which they were deployed. At this point, the device 102' is no longer anchored to the head portion of the bone such that the device 102' may be removed therefrom.

It will be apparent to those skilled in the art that various modifications and variations may be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A method for treating a bone, comprising:
   inserting a device to a desired position within a head portion of a target bone, the device including an elongated body having a lumen extending therethrough and a deploying member movably received within the lumen, the deploying member being coupled to a plurality of wires which, in an insertion configuration, are received within the lumen;
   moving the deploying member relative to the lumen to drive the wires distally out of the lumen so that the wires penetrate a portion of bone adjacent to a distal end of the elongated body to anchor the device to the target bone; and
   coupling the device to a bone stabilization implant coupled to an exterior of the target bone,
   wherein the wires are coupled to the deploying member via protrusions at proximal ends thereof.

2. The method of claim 1, wherein inserting the device to the desired position includes rotating the device about a longitudinal axis thereof.

3. The method of claim 2, wherein the device is a screw coupled to the bone stabilization implant via a threading about a head portion of the screw.

4. The method of claim 1, wherein the wires are moved distally out of the lumen along a curved path.

5. A method for treating a bone, comprising:
   inserting a device to a desired position within a head portion of a target bone, the device including an elongated body having a lumen extending therethrough and a deploying member movably received within the lumen, the deploying member being coupled to a plurality of wires which, in an insertion configuration, are received within the lumen;
   moving the deploying member relative to the lumen to drive the wires distally out of the lumen so that the wires penetrate a portion of bone adjacent to a distal end of the elongated body to anchor the device to the target bone, the deploying member extending distally out of the lumen; and
   coupling the device to a bone stabilization implant coupled to an exterior of the target bone,
   wherein first and second ones of the wires are biased toward an anchoring shape in which distal portions thereof curve radially outward relative to a longitudinal axis of the elongated body, and
   wherein, when in the anchoring shape, the wires curve through an angle between 90 and 180 degrees.

6. A method for treating a bone, comprising:
   inserting a device to a desired position within a head portion of a target bone, the device including an elongated body having a lumen extending therethrough and a deploying member movably received within the lumen, the deploying member being coupled to a plurality of wires which, in an insertion configuration, are received within the lumen;
   moving the deploying member relative to the lumen to drive the wires distally out of the lumen so that the wires penetrate a portion of bone adjacent to a distal end of the elongated body to anchor the device to the target bone, the deploying member extending distally out of the lumen; and
   coupling the device to a bone stabilization implant coupled to an exterior of the target bone,
   wherein the deploying member is a bolt threadedly engaging an inner surface of the longitudinal body defining the lumen, rotation of the bolt in a first direction relative to a longitudinal axis of the longitudinal body, moving the bolt longitudinally through the lumen.

7. The method of claim 6, further comprising removing the device from the target bone by rotating the bolt in a second direction relative to a longitudinal axis of the elongated body so that the wires are retracted into the lumen of the elongated body.

8. The method of claim 1, wherein the bone stabilization implant is one of a bone plate, a nail and an anchoring element.

* * * * *